US009408837B2

(12) United States Patent
Hoyle et al.

(10) Patent No.: US 9,408,837 B2
(45) Date of Patent: *Aug. 9, 2016

(54) AMELIORATING DRUG-INDUCED ELEVATIONS IN BLOOD PRESSURE BY ADJUNCTIVE USE OF ANTIHYPERTENSIVE DRUGS

(75) Inventors: Peter C. Hoyle, Lovettsville, VA (US); Paul Waymack, Washington, DC (US)

(73) Assignee: Kitov Pharmaceutical Ltd., Jerusalem (IL)

( * ) Notice: Subject to any disclaimer, the term of this patent is extended or adjusted under 35 U.S.C. 154(b) by 282 days.

This patent is subject to a terminal disclaimer.

(21) Appl. No.: 13/026,741

(22) Filed: Feb. 14, 2011

(65) Prior Publication Data
US 2011/0136793 A1 Jun. 9, 2011

Related U.S. Application Data

(63) Continuation-in-part of application No. 12/990,724, filed as application No. PCT/US2009/044966 on May 22, 2009.

(60) Provisional application No. 61/304,243, filed on Feb. 12, 2010, provisional application No. 61/320,477, filed on Apr. 2, 2010, provisional application No. 61/056,789, filed on May 28, 2008, provisional application No. 61/097,972, filed on Sep. 18, 2008.

(51) Int. Cl.
| | | |
|---|---|---|
| A61K 31/18 | (2006.01) |
| A61K 31/192 | (2006.01) |
| A61K 31/415 | (2006.01) |
| A61K 31/4439 | (2006.01) |
| A61K 31/4418 | (2006.01) |
| A61K 31/165 | (2006.01) |
| A61K 31/5377 | (2006.01) |
| A61K 31/4422 | (2006.01) |
| A61K 31/137 | (2006.01) |
| A61K 31/549 | (2006.01) |
| A61K 9/00 | (2006.01) |
| A61K 31/635 | (2006.01) |
| A61K 47/12 | (2006.01) |
| A61K 47/26 | (2006.01) |
| A61K 47/36 | (2006.01) |

(52) U.S. Cl.
CPC ........... *A61K 31/4422* (2013.01); *A61K 9/0053* (2013.01); *A61K 31/137* (2013.01); *A61K 31/165* (2013.01); *A61K 31/192* (2013.01); *A61K 31/4418* (2013.01); *A61K 31/549* (2013.01); *A61K 31/635* (2013.01); *A61K 47/12* (2013.01); *A61K 47/26* (2013.01); *A61K 47/36* (2013.01); *A61K 31/18* (2013.01)

(58) Field of Classification Search
CPC .............. A61K 31/292; A61K 31/415; A61K 31/4439; A61K 31/4418; A61K 31/5377; A61K 31/165; A61K 31/18
See application file for complete search history.

(56) References Cited

U.S. PATENT DOCUMENTS

| | | | |
|---|---|---|---|
| 6,057,344 A * | 5/2000 | Young ............................ 514/356 |
| 6,323,226 B1 | 11/2001 | Delgado et al. |
| 2004/0186155 A1 | 9/2004 | Dayno et al. |
| 2006/0160834 A1 | 7/2006 | Fong et al. |
| 2006/0177504 A1 | 8/2006 | Sundharadas |

FOREIGN PATENT DOCUMENTS

| WO | 2006102476 | 9/2006 |
|---|---|---|
| WO | WO 2007-021460 | 2/2007 |

OTHER PUBLICATIONS

Huston. M. C., "Nonsteroidal anti-inflammatory drugs and antihypertensives". American Journal of medicine, Excerpta Medica, Inc, United States. vol. 90, No. 5, May 17, 1991. pp. S42-S47, XP023307988, ISSN: 0002-9343.

Arellano, F.M., et al., "Use of Cyclo-oxygenase 2 inhibitors (COX-2) and prescription non-steroidal anti-inflammatory drugs (NSAIDS) in UK and USA populations. Implication for COX-2 cardiovascular profile." Pharmacoepidemiology and Drug Safety. 2006, vol. 15, No. 12, pp. 861-872, ISSN 1053-8569, See the whole document.

Huerta, C., et al., "Nonsteroidal anti-inflammatory drugs and risks of ARF in the general population." American Journal of Kidney Disease. 2005, vol. 45, No. 3, pp. 531-539, ISSN 0272-6386, See the whole document.

(Continued)

*Primary Examiner* — Samira Jean-Louis
(74) *Attorney, Agent, or Firm* — Whitham, Curtis & Cook, P.C.

(57) ABSTRACT

Patients which are treated with stimulants (e.g., CNS stimulants, sympathomimetic amine, or anorectic/anorexigenic), such as patients being treated for attention deficit/hyperactivity disorder or obesity, often are atrisk in developing high blood pressure. Similarly, patients which are treated with analgesics such as non-steroidal anti-inflammatory drugs (NSAIDs) over an extended period of time risk developing high blood pressure. These and other iatrogenic therapies (therapies which inadvertently cause an increase in, e.g., blood pressure) are addressed by providing the patient with one or more antihypertensive drugs, most preferably calcium channel blockers, during the treatment period. The CNS or NSAIDs can be provided separately or together with the antihypertensive drugs or as part of a combined composition. The adjunctive therapy can prevent or reduces cardiovascular disease and other complications of high blood pressure attendant with these iatrogenic therapies.

3 Claims, No Drawings

(56) References Cited

OTHER PUBLICATIONS

Verberk et al., "The Applicability of Home Blood Pressure Measurement in Clinical Practice: A Review of Literature" Vascular Health and Risk Management, 2007, vol. 3, No. 6, p. 959-966.

Dolan et al., "Superiority of Ambulatory Over Clinic Blood Pressure Measurement in Predicting Mortality: The Dublin Outcome Study" Hypertension, Jun. 6, 2005, vol. 46, p. 156-161.

Boeckxstaens et al., "A Practice-Based Analysis of Combinations of Diseases in Patients Aged 65 or Older in Primary Care", BMC Family Practice, 2014, vol. 15, No. 159, p. Entire Article.

Abe et al., "Indomethacin Inhibits the Antihypertensive Effect of Captopril, SQ 14225, in Low Renin Hypertension", Tohoku J. Exp. Med., 1980, vol. 132, p. 117-118.

Solomon et al., "Cardiovascular Risk Associated with Celecoxib in a Clinical Trial for Colorectal Adenoma Prevention", The New England Journal of Medicine, Mar. 17, 2005, vol. 352, No. 11, p. 1071-1080.

Brewster et al., "Why do Hypertensive Patients of African Ancestry Respond Better to Calcium Blockers and Diuretics than to ACE Inhibitors and SS-Adrenergic Blockers? A Systematic Review" BMC Medicine, 2013, vol. 11, No. 141, p. Entire Article.

Whelton et al., "Effects of Celecoxib and Rofecoxib on Blood Pressure and Edema in Patients >65 Years of Age with Systemic Hypertension and Osteoarthritis", The American Journal of Cadiology, Nov. 1, 2002, vol. 90, p. 959-963.

Trelle et al., "Cardiovascular safety of Non-Steroidal Anti-Inflammatory Drugs: Network Meta-Analysis", BMJ, 2011, vol. 342, No. 7086, p. Entire Article.

FDA Labeling document for CELEBREX.

Whelton et al., Cardiorenal effects of celecoxib as compared with the nonsteroidal anti-inflammatory drugs diclofenac and ibuprofen, Kidney International (2006) 70, 1495-1502.

Morgan et al., the effect of nonsteroidal anti-inflammatory drugs on blood pressure in patients treated with different antihypertensive drugs, The Journal of Clinical Hypertension, (2003) vol. V, No. 1.

Polonia et al., Influence of non-steroidal anti-inflammatory drugs on renal function and 24h ambulatory blood pressure-reducing effects of enalapril and nifedipine gastrointestinal therapeutic system in hypertensive patients, J Hypertens. 1995, 13(8):925-31.

Whelton et al., Effects of celecoxib and rofecoxib on blood pressure and edema in patients > or =65 years of age with systemic hypertension and osteoarthritis, Am J Cardiol. 2002, 90(9):959-63.

2004 FDA Labeling document for CELEBREX.

Transcript from Day 1 of a 2005 FDA meeting.

* cited by examiner

AMELIORATING DRUG-INDUCED ELEVATIONS IN BLOOD PRESSURE BY ADJUNCTIVE USE OF ANTIHYPERTENSIVE DRUGS

CROSS-REFERENCE TO RELATED APPLICATIONS

This application claims priority to U.S. Provisional Patent Application 61/304,243 filed Feb. 12, 2010 and U.S. Provisional Patent Application 61/320,477 filed Apr. 2, 2010, and the complete contents of these applications is herein incorporated by reference. This application is also a continuation-in-part of U.S. patent application Ser. No. 12/990,724 filed Nov. 2, 2010, which is a national stage patent filing of PCT/US2009/044966 filed May 22, 2009, which claims priority to U.S. Provisional Patent Application 61/097,972 filed Sep. 18, 2008 and U.S. Provisional Patent Application 61/056,789 filed May 28, 2008, and the complete contents of each of these applications is herein incorporated by reference.

FIELD OF THE INVENTION

The invention is related to the adjunctive use of one or more antihypertensive drugs (e.g., preferably calcium channel blockers or beta blockers) to ameliorate drug-induced elevations in blood pressure which are symptomatic of stimulant, analgesic, and antipyretic therapies. The invention will thus assist in preventing or reducing adverse cardiovascular side effects (e.g., stroke, heart disease, etc.) which may result from high blood pressure.

BACKGROUND OF THE INVENTION

The cyclooxygenase (COX) system includes a ubiquitous set of enzymes that are present throughout the human body and that initiate the biochemical conversion of arachidonic acid into various physiologically active metabolites, including various prostaglandins.[1] These metabolites can increase or decrease immune function, increase or decrease the propensity of blood to clot, vasodilate blood vessels or vasoconstrict the vessels. They also protect the lining of the gastrointestinal (GI) tract against ulceration.

One of the prostaglandins (prostaglandin E) also affects renal (kidney) function. It decreases renal tubular absorption of sodium, thereby increasing sodium excretion; inadequate sodium excretion causes fluid retention, and thereby causes hypertension (high blood pressure).[2] Thus, anything that decreases prostaglandin E production can be expected to increase blood pressure.

Whenever the body suffers an injury, the COX system increases the production of inflammatory metabolites, including prostaglandin E. The increased levels of prostaglandin E then stimulate immune function and inflammation.[3] As a result of these effects, prostaglandin E causes and increases the amount of pain a patient experiences following externally induced injuries such as broken bones, or internally induced injuries such as headaches. It also causes pain in chronic conditions such as arthritis.

In light of the importance of the prostaglandins in the generation of pain, a number of analgesic drugs have been developed over the years to block the production of prostaglandin E, and thereby to decrease the amount of pain the patient experiences. These analgesic drugs, that work by primarily blocking the COX enzyme system, are referred to as NSAIDs.

NSAIDs that block both the COX-1 and COX-2 enzymes are often referred to generally as non-selective NSAIDs. NSAIDs that block preferentially the COX-2 enzyme are referred to generally as COX-2 inhibitors.

The Merck Manual, 16th Edition, Merck Research Laboratories (1990) pp 1308-1309 provides well known examples of NSAIDs[4]. The term NSAIDs includes, but is not limited to, the group consisting of salicylates, indomethacin, flurbiprofen, diclofenac, ketorolac, naproxen, piroxicam, tebufelone, ibuprofen, etodolac, nahumetone, tenidap, alcofenac, antipyrine, aminopyrine, dipyrone, aminopyrone, phenylbutazone, clofezone, oxyphenbutazone, prexazone, apazone, benzydamine, bucolome, cinchopen, clonixin, ditrazol, epirizole, fenoprofen, floctafeninl, flufenamic acid, glaphenine, indoprofen, ketoprofen, meclofenamic acid, mefenamic acid, niflumic acid, phenacetin, salidifamides, sulindac, suprofen and tolmetin. The salicylates may include acetylsalicylic acid, sodium acetylsalicylic acid, calcium acetylsalicylic acid, salicylic acid, and sodium salicylate.

These analgesics are the most widely consumed pharmaceuticals in the U.S. Although most patients take them for only brief durations of time while treating conditions such as headache or muscle pains, other patients with chronic diseases, such as arthritis, remain on them for months or years.

The non-selective NSAIDs approved by the Food and Drug Administration (FDA) for marketing include indomethacin, ibuprofen, naproxen, etodolac, nabumetone, diclofenac, ketoprofen, and piroxicam. FDA approved COX-2 inhibitors have included valdecoxib, rofecoxib, and celecoxib. All of these NSAIDs have been documented to be extremely effective in reducing pain. However, as a result of their inhibition of the synthesis of prostaglandins, NSAIDs can cause multiple serious problems (adverse reactions).

The most widely recognized problem resulting from NSAIDs that block the COX enzyme system is GI ulcerations. The FDA has estimated that between 10,000 and 20,000 patients in the U.S. per year die from complications resulting from GI ulcerations resulting from these drugs.[5] To prevent these GI ulcerations, physicians have prescribed a number of anti-ulcer medications. These include antacids, proton pump inhibitors, and histamine $H_2$-receptor (H-2) blockers.

A subset of the NSAID family, the COX-2 inhibitors, was developed in the hopes that they would be less likely to result in GI ulcerations. The COX-2 inhibitors were developed to block only one of the COX enzymes: the COX-2 enzyme. The COX-2 inhibitors do not block the COX-1 enzyme. Since the COX-1 enzyme is present in the lining of the GI tract, but the COX-2 enzyme is not, it was anticipated that a drug that selectively blocks the COX-2 enzyme would result in less GI toxicity while still alleviating pain. This was found to be the case and thus, beginning in the late 1990s, FDA approved a number of selective COX-2 inhibitors for marketing in the U.S. including rofecoxib, valdecoxib, and celecoxib. Other COX-2 inhibitors include, but are not limited to paracoxib, etoricoxib, and lumiracoxib.

Recently, the potential for NSAIDs, including COX-2 inhibitors, to he associated with severe cardiovascular problems has been recognized. This recognition has led to the drug rofecoxib being removed from the market and to the FDA requiring a boxed warning—boxed warnings are FDA's strongest warnings contained within a drug's labeling—for all NSAIDs, including COX-2 inhibitors. This boxed warning informs physicians that these drugs may cause myocardial infarctions (heart attacks), and other cardiovascular complications.

The FDA summarized its position on the risks to the cardiovascular system from NSAIDs, including COX-2 inhibitors, in a memorandum from John Jenkins and Paul Seligman through Steve Galson (the FDA's Acting Director for the Center for Drug Evaluation and Research) to the New Drug Application files for the various drugs at issue.[6] Currently, the FDA has taken the position that it does not know the etiology by which NSAIDs, including COX-2 inhibitors, increase the risk for myocardial infarctions and other cardiovascular complications. The FDA has noted that the increased rate of myocardial infarctions among patients taking NSAIDs, including COX-2 inhibitors, does not occur until the patients have been receiving the drugs for many months. The FDA has also stated that it is unable to discern any difference in risk among the various approved NSAIDs, including COX-2 inhibitors.

A meta-analysis of randomized clinical trials of various NSAIDs has documented that these drugs increase blood pressure.[7] The amount of the increase reported in this meta-analysis varied slightly depending upon the specific NSAID (no COX-2 inhibitors were reviewed in this meta-analysis). Overall, the increase in mean blood pressure was 5.0 mm Hg. This level of hypertension is significantly less than that seen in essential hypertension—essential hypertension is the common form of hypertension that occurs for no known reason— but still represents a potential health risk. For example, an increase in mean blood pressure of only 5.0 mm Hg may not seem excessive, but it has been repelled that such an increase, even when over a less than chronic period of time, increased the risk of stroke by 67% and of cardiac disease by 15%.[8] To that end, prevention of NSAID-induced hypertension can be expected potentially to have major benefits to the health of the millions of Americans who take these medications.

This increased risk of hypertension among patients taking various NSAIDs includes the COX-2 inhibitors. Specifically, the FDA approved drug labeling for the COX-2 inhibitor rofecoxib listed high blood pressure as occurring more frequently in rofecoxib treated patients than in placebo control patients. It should be noted that the FDA approved drug labeling for celecoxib also describes an increased rate of hypertension in patients receiving the drug.

The hypertension resulting from NSAIDs can be expected to affect other parts of the cardiorenal system. These other effects would include edema formation and potentially congestive heart failure. It is thus not surprising that a recent epidemiology study conducted using the United Kingdom's General Practice Research Database documented that patients started on NSAIDs had a 1.6 relative risk (a 60% increased risk compared to patients not receiving the drugs) of being diagnosed with clinical heart failure compared to patients of the same age not started on such drugs.[9]

To summarize, clinical data have indicated that the use of NSAIDs, including COX-2 inhibitors, are associated with hypertension, myocardial infarctions, and death. However, to date, no effective mechanism for prophylactically addressing these etiologies has been developed.

CNS stimulants have been utilized for decades to treat primarily two conditions: obesity and ADHD. These drugs increase CNS activity.

Stimulants, also referred to as sympathomimetics, include but are not limited to phentermine, diethylpropion, methamphetamine, dextroamphetamine, methylphenidate, lisdexamphetamine, modafinil, pemoline, dexmethylphenidate, phendimetrazine, benzphetamine, and their salts and prodrugs.

Among the areas of the brain stimulated by CNS stimulants are the brain's satiety center. As a result, CNS stimulants reduce appetite. As a result of the decreased appetite, varying amounts of weight loss occur while patients are on these therapies.[10]

Being overweight as well as suffering outright obesity increase the risk of multiple medical conditions. Thus, weight loss is a highly desirable outcome. Unfortunately, weight loss is difficult to achieve without medical or surgical intervention. Medical intervention includes the use of CNS stimulants that reduce appetite.

The FDA has approved CNS stimulants for weight loss. These include phentermine and simbutramine. Both of these agents, while effective in assisting in weight loss, possess serious cardiovascular adverse effects that are included in the drug labeling warnings and will be discussed in greater detail later.

ADHD is a psychiatric diagnosis listed in the Diagnostic and Statistics Manual IV. It includes an increased level of activity in the patient. This increased level of activity impairs the patient's ability to conduct normal daily functions. Such functions can include employment duties and schooling requirements. To that end, it can interfere with the ability to lead a normal productive life.

CNS stimulants improve behavior in patients suffering from ADHD.[11,12] This improvement results in enhanced performance in a number of situations including school performance and job performance.

A number of CNS stimulants have been approved by the FDA for the treatment of ADHD and other disorders. These drugs include methylphenidate, d-methylphenidate, amphetamine, dextroamphetamine, and mondafinil.

Although CNS stimulants have been documented to be effective in treating ADHD and in causing weight loss, they do possess significant side effects: including cardiovascular side effects.[13] These cardiovascular side effects have resulted in bolded warnings in the labeling of the CNS stimulants.

The hypertensive effect of CNS stimulants has been well recognized in both adults and children.[14,15,16,17] These publications document a 3 to 7 torr increase in systolic blood pressure while on stimulant therapy. They also document a statistically significant increase in heart rate: 2 to 8 bpm. The combination of an increased cardiac rate plus an increase in blood pressure results in a significant increase in the cardiac workload.

The increase in blood pressure and cardiac rate with CNS stimulants appears to have clinical significance as evidenced by an increased rate of hospitalizations for cardiac problems[17] and an increased risk of sudden death[13]. To that end, these data and analyses indicate an unmet need for a safer drug product for the treatment of ADHD. Some CNS stimulants have been removed from the market due to the cardiovascular risks they have been found to possess. These include fenfluramine and dexfenfluramine.

SUMMARY

According to the invention, antihypertensive drugs, such as calcium channel blockers or beta blockers, are used to reduce (i.e., ameliorate) drug-induced blood pressure increases in patients that receive therapies that include the administration of stimulants or NSAIDs. This therapy, which counteracts iatrogenic therapies which result in elevated blood pressure, reduces the risk of serious cardiovascular complications, including heart attack, stroke, and death in these patients. To ameliorate elevations in blood pressure via the adjunctive use of at least one antihypertensive drug, the antihypertensive drug should be administered at the same time as the stimulants or NSAIDs (or other iatrogenic therapy). That is, these drugs might be taken during the same day or at the same time or approximately the same time throughout the course of treatment with stimulants or NSAIDs. In one embodiment, the antihypertensive might by compounded with or otherwise be combined with the stimulant or NSAID in order for the patient to conveniently take them together.

In one embodiment, an oral dosage form includes a therapeutically effective amount of a stimulant, including but not limited to a central nervous system (CNS) stimulant, or a sympathomimetic amine, or anorectic/anorexigenic, and one or more antihypertensive drugs (e.g., calcium channel blocking or beta blocking drugs) in an amount effective to prevent or reduce cardiovascular side effects normally associated with the stimulant. These cardiovascular side effects include, but are not limited to high blood pressure, increase in heart rate, heart attack, stroke, ophthalmologic complications, and death.

In another embodiment, the invention provides a method of treating a human patient in need of antiinflammatory, analgesic and/or antipyretic therapy, or therapy for attention deficit/hyperactivity disorder (ADHD), or treatment for obesity. This embodiment of the invention includes orally administering to the patient, for example, an oral pharmaceutical dosage form that includes a therapeutically effective amount of a non-steroidal anti-inflammatory drug (NSAID), or CNS stimulant, and an amount of one or more antihypertensive drugs (e.g., calcium channel or beta blocking drugs) effective substantially to prevent or reduce cardiovascular side effects of the therapy.

In yet another embodiment, the invention provides a method of prophylactically treating a human patient who is or will be on a therapy, including drug therapy or other practices of medicine, referred collectively to as "iatrogenic therapy", known to have significant cardiovascular side effects. This embodiment includes orally administering to the patient adjunctive therapy with one or more antihypertensive drugs (e.g., calcium channel or beta blocking drugs) so as to prevent or reduce the elevation in blood pressure and/or heart rate induced by the therapy known to have significant cardiovascular side effects.

DETAILED DESCRIPTION

Elevations in blood pressure can lead to a number of serious clinical conditions. These include, stroke, myocardial infarction, renal failure, and ophthalmological complications.[18] To prevent such serious complications, antihypertensive drugs are widely prescribed to patients with hypertension.

There are multiple types of antihypertensive drugs available to physicians.[19] These include, but are not limited to alpha blockers, beta blockers, calcium channel blockers, angiotensin converting enzyme (ACE) inhibitors, angiotensin-receptor antagonists, and diuretics. Except for the diuretics, these agents work primarily by dilating (relaxing) the body's arteries.

In one embodiment of this invention, drug-induced elevations in blood pressure caused by, for example, the repetitive administration of stimulants for the treatment of ADHD or obesity or the repetitive administration of NSAIDs (including non-specific NSAIDs and COX-2 inhibitors) to achieve analgesic or antipyretic therapy, can be effectively ameliorated by the administration of antihypertensive drugs (calcium channel blockers and beta blockers being particularly preferred). In the practice of the invention, the stimulants or NSAIDs can be any of those referenced above as well as any other stimulant or NSAID now known or identified in the future. Examples of antihypertensive drugs which may be used in the present invention include:

Alpha blockers, also referred to as alpha-adrenoceptor antagonists, include but are not limited to prazosin, terazosin, doxazosin, trimazosin, phentolamine, and phenoxybenzamine.

Beta blockers, also referred to as beta-adrenergic blocking agents, include but are not limited to metoprolol, betaxolol, propranolol, nadolol, atenolol, carvedilol, labetalol, sotalol, and timolol.

Calcium channel blockers include but are not limited to amlodipine, diltiazem, nimodipine, verapamil, felodipine, and isradipine.

ACE inhibitors include but are not limited to trandolapril, fosinopril, enalapril, lisinopril, ramipril, captopril, quinapril, perindopril, and benazepril.

Angiotensin receptor antagonists, also referred to as angiotensin II inhibitors, include but are not limited to eprosartan, olmesartan, telmisartan, candesartan, losartan, valsartan, and irbesartan.

Diuretics include but are not limited to carbonic anhydrase inhibitors (e.g., acetazolamide, dichlorphenamide, and methazolamide), loop diuretics (e.g., torsemide, furosemide, bumetanide, and ethacrynic acid), potassium-sparing diuretics (e.g., spironolactone, amiloride, and triamterene), thiazide diuretics (e.g., hydrochlorothiazide, indapamide, methyclothiazide, and metolazone), and other types (e.g., pamabrom and mannitol).

As the arteries relax, the tension within the artery decreases and with it the patient's blood pressure. The ability of antihypertensive drugs to reduce blood pressure in patients with elevated blood pressure reduces the risk of serious cardiovascular complications, including heart attack, stroke, and death in these patients. To ameliorate elevations in blood pressure via the adjunctive use of at least one antihypertensive drug, the antihypertensive drug should be administered at the same time as the stimulants or NSAIDs (or other iatrogenic therapy). That is, these drugs might be taken during the same day or at the same time or approximately the same time throughout the course of treatment with stimulants or NSAIDs. In one embodiment, the antihypertensive might by compounded with or otherwise be combined with the stimulant or NSAID in order for the patient to conveniently take them together.

Preventing, via the Use of CNS Stimulant Combinations with Antihypertensive Drugs, Cardiovascular/Renal Complications Due to CNS Stimulants It has been clearly established that the use of various CNS stimulants are associated with an increased incidence of various cardiovascular complications, including elevated blood pressure, increased heart rate, myocardial infarction, congestive heart failure, and death. The myocardial infarctions and deaths may, and probably are, the result of the propensity of these drugs to elevate blood pressure and heart rate. If these two complications cause all the other problems, then most of these other problems should be preventable in most patients by administering an antihypertensive drug to patients taking any of the various CNS stimulants.

By preventing the elevation in blood pressure and heart rate over a period of weeks, months, or years, the combining of an antihypertensive drug with the various CNS stimulants can he expected to reduce the risk of other cardiovascular complications, heart attack, stroke and death. This means that the problems the FDA has identified from the use of CNS stimulants, and that have lead FDA to include warnings in the labeling of CNS stimulants, may be prevented.

It should be noted that antihypertensive drugs have been widely prescribed for many decades and are thus recognized as being generally safe for patients.[20] They have also been documented to decrease the risk of myocardial infarction and stroke in patients suffering from essential (non-drug induced) hypertension.[18] Thus, the theoretical risk/benefit ratio from adding one or more antihypertensive drugs to a CNS stimulant would be potentially significant.

CNS stimulants are among the most widely consumed group of drugs in the US, and one of the most widely consumed drugs worldwide. Thus, reducing the adverse cardiovascular effects of CNS stimulants by combination with one or more antihypertensive drugs could potentially be a major benefit for the patients consuming CNS stimulants.

In light of all these facts, it is proposed that a combination drug therapy of one or more CNS stimulants and one or more antihypertensive drugs will provide the benefits of the CNS stimulants while avoiding the damaging etiologies associated with CNS stimulants and will be in compliance with FDA regulations as necessary. Further, antihypertensive drugs (e.g., calcium channel blockers such as amlodipine and isradipine) can be provided as adjunctive therapy to patients that are being treated with CNS stimulants (as is discussed in more detail below).

Selection of the drug combination will depend on the evaluation of a variety of factors including chemistry, manufacturing and controls (CMC) investigations, nonclinical (animal) pharmacology, pharmacokinetic, and toxicology studies, and clinical (human) studies. The human studies will be conducted under Investigational New Drug applications (INDs), which will require FDA approval. The human studies will be designed to show that for certain combinations of drugs and their application, the administration of an antihypertensive drug with CNS stimulants prevents these adverse cardiovascular complications.

The human studies will randomize patients to receive either the CNS stimulant alone, or the CNS stimulant plus the antihypertensive drug. Patients will be administered these drugs for up to five years. Patients will undergo extensive monitoring during that time. The parameters monitored will include cardiovascular parameter such as blood pressure and heart rate, as well as the incidence of myocardial infarctions, strokes and death. The results between those receiving CNS stimulants alone versus those receiving these drugs plus an antihypertensive drug will be compared using standard biostatistical tests.

The studies will demonstrate that the patients receiving only the CNS stimulants will exhibit a greater elevation in blood pressure compared to those receiving CNS stimulants plus an antihypertensive drug. These differences should become apparent within weeks of initiation of the drug therapy. It is also anticipated that the data from longer-term observations will document a greater rate of myocardial infarction, stroke, and death among patients receiving CNS stimulants alone compared to those receiving CNS stimulants plus an antihypertensive after several years of therapy.

The antihypertensive drugs currently on the market, and the dosing regimens specified for these drugs in their FDA approved labeling, were approved for treating conditions such as essential hypertension. Since these conditions are different from CNS stimulant-induced elevations in blood pressure and heart rate that the combination drug will prevent, it is probable that a different dose of the antihypertensive drugs will be required in order to optimally prevent CNS stimulant-induced elevations in blood pressure and heart rate. To that end, the clinical studies will also assist in delineating the optimal dose of the antihypertensive drugs for this new use.

The optimal dose of the antihypertensive drug for this new use may be determined to be a dose that is lower or higher than the currently labeled range of daily doses and thus use dosage strengths in the combination drug formulation, such as tablets, that are lower or higher than the currently marketed dosage strengths. For example, the optimal daily dose of amlodipine for this new use may be 0.1 mg (or lower) to 1 mg, or 0.5 mg to 2.4 mg, depending on the CNS stimulant or NSAID that amlodipine is administered with. These doses are lower than the lowest labeled dose of amlodipine, and would require a lower dosage strength combination formulation than the lowest currently marketed dosage strength. Similarly, the optimal daily dose of amlodipine for this new use might be 10.1 mg to 15 mg, or 14 mg to 25 mg (or more), depending on the CNS stimulant or NSAID that amlodipine is administered with. These doses are higher than the lowest labeled dose of amlodipine, and might require a higher dosage strength formulation than the highest marketed dosage strength. The above quantitative description of the optimal lower or lower doses of the antihypertensive might apply similarly to any other antihypertensive drug used for this new use (such as isradipine or other calcium channel blockers).

It is anticipated that the FDA approved labeling for such combination drug products will list in their indications section, not only the current labeling indications for the CNS stimulants, but also that the combination reduces CNS stimulant-induced elevations in blood pressure, and elsewhere in the labeling state that a reduction in blood pressure reduces the risk of serious cardiovascular adverse reactions.

Preventing, via Adjunctive Therapy with Antihypertensive Drugs, Cardiovascular/Renal Complications Due to CNS Stimulants It has been clearly established that the use of various CNS stimulants are associated with an increased incidence of various cardiovascular complications, including elevated blood pressure, increased heart rate, myocardial infarction, congestive heart failure, and death. The myocardial infarctions and deaths may, and probably are, the result of the propensity of these drugs to elevate blood pressure and heart rate. If these two complications cause all the other problems, then most of these other problems should be preventable in most patients by administering an antihypertensive drug as adjunctive therapy to patients taking any of the various CNS stimulants.

By preventing the elevation in blood pressure and heart rate over a period of weeks, months, or years, the use of antihypertensive adjunctive therapy with the various CNS stimulants can be expected to reduce the risk of other cardiovascular complications, heart attack, stroke and death. This means that the problems the FDA has identified from the use of CNS stimulants, and that have lead FDA to include warnings in the labeling of CNS stimulants, may be prevented.

It should be noted that antihypertensive drugs have been widely prescribed for many decades and are thus recognized as being generally safe for patients.[20] They have also been documented to decrease the risk of myocardial infarction and stroke in patients suffering from essential (non-drug induced) hypertension.[18] Thus, the theoretical risk/benefit ratio from the use of one or more antihypertensive drugs as adjunctive therapy with a CNS stimulant would be potentially significant.

CNS stimulants are among the most widely consumed group of drugs in the US, and one of the most widely consumed drugs worldwide. Thus, reducing the adverse cardiovascular effects of CNS stimulants via adjunctive therapy with one or more antihypertensive drugs could potentially be a major benefit for the patients consuming CNS stimulants.

In light of all these facts, it is proposed that drug therapy with one or more CNS stimulants and adjunctive therapy with one or more antihypertensive drugs will provide the benefits of the CNS stimulants while avoiding the damaging etiologies associated with CNS stimulants and will be in compliance with FDA regulations as necessary.

Selection of the primary drug and adjunctive therapy will depend on the evaluation of a variety of factors including CMC investigations, nonclinical (animal) pharmacology, pharmacokinetic, and toxicology studies, and clinical (human) studies. The human studies will be conducted under INDs, which will require FDA approval. The human studies will be designed to show that for certain primary and adjunctive therapies and their application, the adjunctive use of an antihypertensive drug with CNS stimulants prevents these adverse cardiovascular complications.

The human studies will randomize patients to receive either the CNS stimulant alone, or the CNS stimulant plus the antihypertensive drug as adjunctive therapy. Patients will be administered these drugs for up to five years. Patients will undergo extensive monitoring during that time. The parameters monitored will include cardiovascular parameters such as blood pressure and heart rate, as well as the incidence of myocardial infarctions, strokes and death. The results between those receiving CNS stimulants alone versus those receiving these drugs plus an antihypertensive drug as adjunctive therapy will be compared using standard biostatistical tests.

The studies will demonstrate that the patients receiving only the CNS stimulants will exhibit a greater elevation in blood pressure compared to those receiving CNS stimulants plus adjunctive therapy with an antihypertensive drug. These differences should become apparent within weeks of initiation of the drug therapy. It is also anticipated that the data from longer-term observations will document a greater rate of myocardial infarction, stroke, and death among patients receiving CNS stimulants alone compared to those receiving antihypertensive adjunctive therapy with the CNS stimulants after several years of therapy.

The antihypertensive drugs currently on the market, and the dosing regimens specified for these drugs in their FDA approved labeling, were approved for treating conditions such as essential hypertension. Since these conditions are different from CNS stimulant-induced elevations in blood pressure and heart rate that the antihypertensive adjunctive therapy will prevent, it is probable that a different dose of the antihypertensive drugs will be required in order to optimally prevent CNS stimulant-induced elevations in blood pressure and heart rate. To that end, clinical studies will assist in delineating the optimal dose of the antihypertensive drugs for use as adjunctive therapy.

The optimal close of the antihypertensive drug for this new use may be determined to be a dose that is lower or higher than the currently labeled range of daily doses and thus use dosage strengths of the dosage formulation, such as tablets, that are lower or higher than the currently marketed dosage strengths. For example, the optimal daily dose of amlodipine for this new use may be 0.1 mg (or lower) to 1 mg, or 0.5 mg to 2.4 mg, depending on the CNS stimulant that amlodipine is administered with. These doses are lower than the lowest labeled dose of amlodipine, and would require a lower dosage strength formulation than the lowest currently marketed dosage strength. Similarly, the optimal daily dose of amlodipine for this new use might be 10.1 mg to 15 mg, or 14 mg to 25 mg (or more), depending on the CNS stimulant that amlodipine is administered with. These doses are higher than the lowest labeled dose of amlodipine, and might require a higher dosage strength formulation than the highest marketed dosage strength. The above quantitative description of the optimal lower or lower doses of the antihypertensive might apply similarly to any other antihypertensive drug used for this new use.

It is anticipated that the FDA approved labeling for the antihypertensive drug used as adjunctive therapy will list in the indications section that adjunctive therapy with the antihypertensive drug reduces CNS stimulant-induced elevations in blood pressure, and elsewhere in the labeling state that a reduction in blood pressure reduces the risk of serious cardiovascular adverse reactions.

Preventing, via Adjunctive Therapy with Antihypertensive Drugs, Cardiovascular/Renal Complications Due to NSAIDs It has been clearly established that the use of various NSAIDs are associated with an increased incidence of various cardiovascular complications, including elevated blood pressure, increased heart rate, myocardial infarction, congestive heart failure, and death. The myocardial infarctions and deaths may, and probably are, the result of the propensity of these drugs to elevate blood pressure and heart rate. If these two complications cause all the other problems, then most of these other problems should be preventable in most patients by administering an antihypertensive drug as adjunctive therapy to patients taking any of the various NSAIDs.

By preventing the elevation in blood pressure and heart rate over a period of weeks, months, or years, the use of antihypertensive adjunctive therapy with the various NSAIDs can he expected to reduce the risk of other cardiovascular complications, heart attack, stroke and death. This means that the problems the FDA has identified from the use of NSAIDs, and that have lead FDA to include warnings in the labeling of NSAIDs, may be prevented.

It should be noted that antihypertensive dnigs have been widely prescribed for many decades and are thus recognized as being generally safe for patients.[20] They have also been documented to decrease the risk of myocardial infarction and stroke in patients suffering from essential (non-drug induced) hypertension.[18] Thus, the theoretical risk/benefit ratio from the use of one or more antihypertensive drugs as adjunctive therapy with NSAIDs would be potentially significant.

NSAIDs are among the most widely consumed group of drugs in the US, and one of the most widely consumed drugs worldwide. Thus, reducing the adverse cardiovascular effects of NSAIDs via adjunctive therapy with one or more antihypertensive drugs could potentially be a major benefit for the patients consuming NSAIDs.

This is especially the case of patients consuming both prescription and non-prescription non-selective NSAIDs (i.e., as opposed to COX-2 inhibitor NSAID). For example, since 2006, only a single COX-2 inhibitor (celecoxib) has been marketed in the U.S. In contrast, multiple non-selective NSAIDs are marketed in the U.S.[21] In part in light of this discrepancy, it has been documented that approximately two-thirds to three-quarters of patients who are prescribed an NSAID by their physician, are prescribed a non-selective NSAID as opposed to a COX-2 inhibitor.[22,23] Thus, the cardiovascular problems seen with all prescription NSAIDs are potentially a greater problem from the non-selective NSAIDs than with the selective COX-2 inhibitor NSAIDs since they are more widely prescribed. Non-selective NSAIDs are also far more widely consumed than COX-2 inhibitors since not only are they prescribed by physicians more frequently, but in addition multiple non-selective NSAIDs are marketed as over-the-counter drugs, which are drugs that can be purchased without obtaining a prescription from a physician. In contrast, there are no COX-2 inhibitors that have been approved for over-the-counter sales. Thus, all over-the-counter NSAIDs consumed in the U.S. are non-selective NSAIDs; no COX-2 inhibitors are consumed from the over-the-counter market.

In light of all these facts, it is proposed that drug therapy with one or more NSAIDs and adjunctive therapy with one or more antihypertensive drugs will provide the benefits of the NSAIDs while avoiding the damaging etiologies associated with NSAIDs and will be in compliance with FDA regulations as necessary.

Selection of the primary drug and adjunctive therapy will depend on the evaluation of a variety of factors including CMC investigations, nonclinical (animal) pharmacology, pharmacokinetic, and toxicology studies, and clinical (human) studies. The human studies will be conducted under INDs, which will require FDA approval. The human studies will be designed to show that for certain primary and adjunctive therapies and their application, the adjunctive use of an antihypertensive drug with NSAIDs prevents these adverse cardiovascular complications.

The human studies will randomize patients to receive either the NSAIDs alone, or the NSAIDs plus the antihypertensive drug as adjunctive therapy. Patients will be administered these drugs for up to five years. Patients will undergo extensive monitoring during that time. The parameters monitored will include cardiovascular parameters such as blood pressure and heart rate, as well as the incidence of myocardial infarctions, strokes and death. The results between those receiving NSAIDs alone versus those receiving NSAIDs plus an antihypertensive drug as adjunctive therapy will be compared using standard biostatistical tests.

The studies will demonstrate that the patients receiving only the NSAIDs will exhibit a greater elevation in blood pressure compared to those receiving NSAIDs plus adjunctive therapy with an antihypertensive drug. These differences should become apparent within weeks of initiation of the drug therapy. It is also anticipated that the data from longer-term observations will document a greater rate of myocardial infarction, stroke, and death among patients receiving NSAIDs alone compared to those receiving antihypertensive adjunctive therapy with the NSAIDs after several years of therapy.

The antihypertensive drugs currently on the market, and the dosing regimens specified for these drugs in their FDA approved labeling, were approved for treating conditions such as essential hypertension. Since these conditions are different from NSAID-induced elevations in blood pressure and heart rate that the antihypertensive adjunctive therapy will prevent, it is probable that a different dose of the antihypertensive drugs will be required in order to optimally prevent NSAID-induced elevations in blood pressure and heart rate. To that end, the clinical studies will also assist in delineating the optimal dose of the antihypertensive drugs for use as adjunctive therapy.

The optimal dose of the antihypertensive drug for this new use may be determined to be a dose that is lower or higher than the currently marketed range of daily doses and thus use dosage strengths of the dosage formulation, such as tablets, that are lower or higher than the currently marketed dosage strengths. For example, the optimal daily dose of amlodipine for this new use may be 0.1 mg (or lower) to 1 mg, or 0.5 mg to 2.4 mg, depending on the NSAID that amlodipine is administered with. These doses are lower than the lowest labeled dose of amlodipine, and would require a lower dosage strength formulation that is lower than the lowest currently marketed dosage strength. Similarly, the optimal daily dose of amlodipine for this new use might be 10.1 mg to 15 mg, or 14 mg to 25 mg (or more), depending on the NSAID that amlodipine is administered with. These doses are higher than the lowest labeled dose of amlodipine, and might require a higher dosage strength formulation than the highest marketed dosage strength. The above quantitative description of the optimal lower or lower doses of the antihypertensive might apply similarly to any other antihypertensive drug used for this new use.

The quantity of amlodipine that will be required to correct the hypertension has not yet been determined. It is anticipated that it may vary depending upon a number of factors. These would include the drug that caused the hypertension: methylphenidate, naproxen, or celecoxib. Each of these drugs may result in varying degrees of hypertension in the patient since each of these drugs is chemically different from the others. Thus, each of these drugs may require a different quantity of amlodipine to correct the hypertension. In addition, some patients may have pre-existing hypertension and thus, require treatment of both their inherent essential hypertension, as well as the drug induced hypertension. This would be especially true of patients being treated with naproxen or celecoxib since these are used chronically, most commonly in osteoarthritis patients and such patients (primarily older patients) are at greater risk of hypertension.

It is anticipated that the FDA approved labeling for the antihypertensive drug used as adjunctive therapy will list in the indications section that adjunctive therapy with the antihypertensive drug reduces NSAID-induced elevations in blood pressure, and elsewhere in the labeling state that a reduction in blood pressure reduces the risk of serious cardiovascular adverse reactions.

Exemplary Embodiments of the Invention for Concurrent Administration of an NSAID, Including a COX-2 Inhibitor, or a Stimulant, and an Antihypertensive Drug in a Combination (Single) Oral Dosage Form or as Separate Dosage Forms In embodiments of the invention, the pharmaceutical compositions containing the antihypertensive and the NSAIDs, including COX-2 inhibitors, or stimulants set forth herein are administered orally. Such oral dosage forms may contain one or both of the drugs in immediate or sustained release form. The oral dosage forms may be in the form of tablets, capsules, troches, lozenges, aqueous or oily suspensions, dispersible powders or granules, emulsions, multiparticulate formulations, syrups, elixirs, and the like.

The combination of the antihypertensive drug and the NSAIDs, including COX-2 inhibitors, or the stimulants can be employed in admixtures with conventional excipients, i.e., pharmaceutically acceptable organic or inorganic carrier substances suitable for oral administration, known to the art. Suitable pharmaceutically acceptable carriers include but are not limited to water, salt solutions, alcohols, gum arabic, vegetable oils, benzyl alcohols, polyethylene glycols, gelate, carbohydrates such as lactose, amylose or starch, magnesium stearate talc, silicic acid, viscous paraffin, perfume oil, fatty acid monoglycerides and diglycerides, pentaerythritol fatty acid esters, hydroxymethylcellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They can also be combined where desired with other active agents, e.g., other analgesic agents. For oral application, particularly suitable are tablets, dragees, liquids, drops, suppositories, or capsules, caplets and gelcaps.

The compositions intended for oral use may be prepared according to any method known in the art and such compositions may contain one or more agents selected from the group consisting of inert, non-toxic pharmaceutically excipients which are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

Aqueous suspensions containing the above-identified combination of drugs may have one or more excipients suitable as suspending agents, for example pharmaceutically acceptable synthetic gums such as hydroxypropylhmethylcellulose or natural gums. Oily suspensions may be formulated by suspending the above-identified combination of drugs in a vegetable oil or mineral oil. The oily suspensions may contain a thickening agent such as beeswax or cetyl alcohol. A syrup, elixir, or the like can be used wherein a sweetened vehicle is employed.

In the case where the antihypertensive drug is to be used as adjunctive therapy with NSAID or stimulant therapy, the pharmaceutical composition of the antihypertensive drug can he formulated in a similar manner to the above combination formulations.

Examples of combination drug formulations containing an antihypertensive drug and an NSAID are as follows:
1. Isradipine formulated with naproxen or extended release naproxen
2. Amlodipine formulated with celecoxib or Celcox
3. Amlodipine formulated with naproxen or extended release naproxen
4. Hydrochlorothiazide formulated with naproxen
5. Atenol or timolol with naproxen or celecoxib Examples of combination drug formulations containing an antihypertensive drug and a stimulant are as follows:
1. Amlodipine formulated with methylphenidate
2. Amlodipine formulated with diethylpropion
3. Amlodipine formulated with methamphetamine
4. Amlodipine formulated with dextroamphetamine
5. Amlodipine formulated with lisdexamphetamine
6. Isradipine formulated with any of methylphenidate, diethylpropion, methamphetamine, dextroamphetamine, or lisdexamphetamine.
7. Amlodipine or Isradipine with Ritalin
8. Atenol or timolol with any of Ritalin, methylphenidate, diethylpropion, methamphetamine, dextroamphetamine, or lisdexamphetamine.

Examples of the use of an antihypertensive drug as adjuvant therapy to reduce drug-induced elevations in blood pressures are as follows:
1. The use of isradipine as adjuvant therapy with naproxen or extended release naproxen
2. The use of amlodipine as adjuvant therapy with celecoxib or Celcox
3. The use of amlodipine as adjuvant therapy with naproxen or extended release naproxen
4. The use of hydrochlorothiazide as adjuvant therapy with naproxen
5. The use of amlodipine as adjuvant therapy with methylphenidate
6. The use of amlodipine as adjuvant therapy with diethylpropion
7. The use of amlodipine as adjuvant therapy with methamphetamine
8. The use of amlodipine as adjuvant therapy with dextroamphetamine
9. The use of amlodipine as adjuvant therapy with lisdexamphetamine
10. The use of isradipine as adjuvant therapy with any of celecoxib, methylphenidate, diethylpropion, methamphetamine, dextroamphetamine, or lisdexamphetamine.
11. The use of amlodipine or isradipine with Ritalin
12. The use of atenolol or timolol with any of Ritalin, methylphenidate, diethylpropion, methamphetamine, dextroamphetamine, or lisdexamphetamine.

As discussed above, the invention contemplates "preventing" cardiovascular and renal complications that are attendant to stimulant therapies which require the administration of one or more stimulants to a subject and particularly to stimulant therapies which require the daily use of one or more stimulants. These complications arc wide ranging and include myocardial infarction, congestive hear failure, stroke, and death. The adjunctive therapy of the present invention includes providing one or more antihypertensive drugs during the stimulant therapy, and preferably providing at least one antihypertensive drug on a daily basis throughout the term of the stimulant therapy. The adjunctive therapy of the present invention will reduce (i.e., ameliorate) stimulant induced blood pressure elevation and/or increased heartbeat. Thus, the adjunctive therapy will either "prevent" (i.e., completely prevent or at least reduce the likelihood) cardiovascular or renal complications in the patient which are attendant with higher blood pressure and faster heart rates.

Similarly, as discussed above, the invention contemplates "preventing" cardiovascular and renal complications that are attendant to anti-inflammatory, analgesic and antipyretic therapies which require the administration of one or more NSAIDs to a subject and particularly to anti-inflammatory, analgesic and antipyretic therapies which require the daily use of one or more NSAIDs. These complications are wide ranging and include myocardial infarction, congestive hear failure, stroke, and death. The adjunctive therapy of the present invention includes providing one or more antihypertensive drugs during the anti-inflammatory, analgesic and antipyretic therapy, and preferably providing at least one antihypertensive drug on a daily basis throughout the term of the anti-inflammatory, analgesic and antipyretic therapy. The adjunctive therapy of the present invention will reduce (i.e., ameliorate) NSAID induced blood pressure elevation and/or increased heartbeat. Thus, the adjunctive therapy will either "prevent" (i.e., completely prevent or at least reduce the likelihood) cardiovascular or renal complications in the patient which are attendant with higher blood pressure and faster heart rates.

While the invention has been described in terms of several exemplary embodiments, those of skill in the art will recognize that the invention can be practiced with variation within the scope of the of the appended claims.

REFERENCES

1. Konturek S J, et al: Physiology and pharmacology of prostaglandins. *Digestive Dis. Sci.* 1986; 31(2 Suppl):6S-19S.
2. Schlondorff D: Renal complications of non-steroidal anti-inflammatory drugs. Kidney International 1993; 44:643-653.
3. Waymack J P, et al: Effect of prostaglandin E in immune function in normal healthy volunteers. Surg. Gyn. Obst. 1992; 175:329-332.

4. Merck Manual, 16$^{th}$ Edition, 1990, Merck Research Laboratories, pp 1308-1309.
5. http://www.fda.gov/ohrms/dockets/ac/01/briefing/3677b2_05_gi.pdf.
6. http://www.fda.gov/ohrms/dockets/ac/06/briefing/2006-4202 B1_09_FDA-Tab09.pdf.
7. Johnson A G, et al: Do nonsteroidal anti-inflammatory drugs affect blood pressure? A meta-analysis. Ann. Internal. Med. 1994; 121:289-300.
8. Collins R, et al: Blood pressure, stroke and coronary heart disease. Part 2. Short-term reductions in blood pressure; overview of randomized drug trials in their epidemiologic context. Lancet 1990; 335:827-838.
9. Rodriguez L A G, et al: Nonsteroidal anti-inflammatory drugs as a trigger of clinical heart failure. Epidemiology 2003; 14:240-246.
10. Padwal R, et al: Long-term pharmacotherapy for obesity and overweight. Cochrane Database Syst. Rev. 2004; (3): CD004094.
11. Biederman J, et al: Long-term safety and effectiveness of mixed amphetamines salts extended release in adults with ADHD. CNS Spectr. 2005; 10(12 Suppl 20):16-25.
12. Wigal S B: Efficacy and safety limitations of attention-deficit hyperactivity disorder pharmacotherapy in children and adults. CNS Drugs 2009; 23(Suppl I):21-31.
13. Department of Health and Human Services Memorandum. Gelperin K, Benoit S, Pamer C: Review of AERS data for marketed safety experience during stimulant therapy: death, sudden death, cardiovascular SAEs (including stroke). Apr. 27, 2004.
14. Hammerness P, et al: Cardiovascular effects of longer-term, high-dose OROS methylphenidate in adolescents with attention deficit hyperactivity disorder. J. Pediatr. 2009; 155:84-89.
15. Wilens T E, et al: Blood pressure changes associated with medication treatment of adults with attention-deficit/hyperactivity disorder. J. Clin. Psychiatry 2005; 66:253-259.
16. Stowe C D, et al: 24-hour ambulatory blood pressure monitoring in male children receiving stimulant therapy. Annals of Pharmacology 2002; 36:1142-1149.
17. Winterstein A G, et al: Cardiac safety of methylphenidate versus amphetamine salts in the treatment of ADHD. Pediatrics 2009; 124Le75-e80.
18. Lewington S, et al: Age-specific relevance of usual blood pressure to vascular mortality: a meta-analysis of individual data for one million adults in 61 prospective studies. Lancet 2002; 360:1903-1913.
19. August P: Initial treatment of hypertension. New Eng. Journal of Med. 2003; 348:610-617.
20. Salvetti A, et al: Thiazide diuretics in the treatment of hypertension: An update. Journal of the Am. Soc. Nephrol. 2006; 17:25-29.
21. Physician's Desk Reference, 61$^{st}$ Edition, 2007, Thomson Publishers.
22. Thompson P W, et al: Long-term NSAID use in primary care: changes over a decade and NICE risk factors for gastrointestinal adverse events. Rheumatology 2005; 44:1308-1310.
23. Sun S X, et al: Withdrawal of COX-2 selective inhibitors rofecoxib and valdecoxib: impact on NSAID and gastroprotective drug prescribing and utilization. Curr. Med. Res. Opin. 2007; 23:1859-66.

The invention claimed is:

1. A method for ameliorating celecoxib-induced elevation of blood pressure in a subject, comprising:
   a. administering at least one dose of celecoxib,
      wherein the at least one dose of celecoxib is sufficient to cause elevation in blood pressure in the subject; and
   b. administering at least one dose of amlodipine at a dosage which is sufficient to ameliorate blood pressure elevation in the subject.

2. A method for ameliorating celecoxib-induced elevation of blood pressure in a subject in need of anti-inflammatory, analgesic, or antipyretic therapy, comprising:
   a. administering at least one dose of celecoxib,
      wherein the at least one dose of celecoxib is sufficient to cause elevation in blood pressure in the subject; and
   b. administering at least one dose of amlodipine at a dosage which is sufficient to ameliorate blood pressure elevation in the subject.

3. A method for ameliorating celecoxib-induced elevation of blood pressure in a subject, comprising:
   providing to a subject at least one dose comprising a combination of celecoxib and amlodipine,
      wherein the amount of celecoxib is sufficient to cause elevation in blood pressure, and
      wherein the amount of amlodipine is sufficient to ameliorate blood pressure elevation.

* * * * *